(12) United States Patent
Purdy et al.

(10) Patent No.: US 11,877,877 B2
(45) Date of Patent: Jan. 23, 2024

(54) IMAGING SYSTEM WITH ADAPTIVE OBJECT MAGNIFICATION

(71) Applicant: FAXITRON BIOPTICS, LLC, Marlborough, MA (US)

(72) Inventors: Ciaran Purdy, Tucson, AZ (US); Mikhail Viznyuk, Tucson, AZ (US); Mehmet Akif Baysal, Tucson, AZ (US)

(73) Assignee: Faxitron Bioptics, LLC, Marlborough, MA (US)

( * ) Notice: Subject to any disclaimer, the term of this patent is extended or adjusted under 35 U.S.C. 154(b) by 0 days.

(21) Appl. No.: 17/712,376

(22) Filed: Apr. 4, 2022

(65) Prior Publication Data
US 2022/0296189 A1 Sep. 22, 2022

Related U.S. Application Data

(63) Continuation of application No. 16/646,379, filed as application No. PCT/US2018/050490 on Sep. 11, 2018, now Pat. No. 11,317,881.

(60) Provisional application No. 62/556,566, filed on Sep. 11, 2017.

(51) Int. Cl.
A61B 6/00 (2006.01)
A61B 6/03 (2006.01)

(52) U.S. Cl.
CPC ............ A61B 6/4411 (2013.01); A61B 6/035 (2013.01); A61B 6/4452 (2013.01); A61B 6/5229 (2013.01)

(58) Field of Classification Search
CPC ..... A61B 6/035; A61B 6/4411; A61B 6/4452; A61B 6/508; A61B 6/5229; G01N 2223/3306; G01N 2223/3308; G01N 2223/6126; G01N 23/046
See application file for complete search history.

(56) References Cited

U.S. PATENT DOCUMENTS

| 4,038,988 | A | 8/1977 | Perisse |
| 4,134,012 | A | 1/1979 | Smallbone et al. |
| 4,306,570 | A | 12/1981 | Matthews |
| 4,549,554 | A | 10/1985 | Markham |
| 4,658,834 | A | 4/1987 | Blankenship et al. |
| 4,802,195 | A | 1/1989 | Wojcienchowski |
| 4,803,639 | A | 2/1989 | Steele |

(Continued)

FOREIGN PATENT DOCUMENTS

| EP | 2007287 | 6/2016 |
| GB | 2018601 | 10/1979 |

(Continued)

OTHER PUBLICATIONS

European Extended Search Report in Application 18853903.5, dated May 17, 2021, 8 pages.

(Continued)

Primary Examiner — Dani Fox
(74) Attorney, Agent, or Firm — Merchant & Gould P.C.

(57) ABSTRACT

An imaging system that is configured to automatically obtain and provide two and three-dimensional digital images of various types of objects (e.g., tissue specimens, animals, electrical devices, etc.) for use in analysis thereof in a manner free of manual repositioning of the objects between images and free of movement of an electromagnetic radiation source and detector within or relative to a cabinet housing of the system.

18 Claims, 10 Drawing Sheets

(56) References Cited

U.S. PATENT DOCUMENTS

| | | |
|---|---|---|
| 4,837,795 A | 6/1989 | Garrigus |
| 4,852,560 A | 8/1989 | Hermann, Jr |
| 5,023,894 A | 6/1991 | Yamashita |
| 5,023,895 A | 6/1991 | McCroskey |
| 5,256,160 A | 10/1993 | Clement |
| 5,427,742 A | 6/1995 | Holland |
| 5,456,689 A | 10/1995 | Kresch et al. |
| 5,491,344 A | 2/1996 | Kenny et al. |
| 5,505,210 A | 4/1996 | Clement |
| 5,526,822 A | 6/1996 | Burbank et al. |
| 5,541,856 A | 7/1996 | Hammermeister |
| 5,575,293 A | 11/1996 | Miller et al. |
| 5,609,827 A | 3/1997 | Russell |
| 5,754,621 A | 5/1998 | Suzuki |
| 5,983,125 A | 11/1999 | Alfano et al. |
| 6,017,316 A | 1/2000 | Ritchart et al. |
| 6,032,673 A | 3/2000 | Savage et al. |
| 6,058,159 A | 5/2000 | Conway |
| 6,163,590 A | 12/2000 | Wilkins |
| 6,207,111 B1 | 3/2001 | Weinberg |
| 6,225,107 B1 | 5/2001 | Nagle |
| 6,234,672 B1 | 5/2001 | Tomasetti et al. |
| 6,322,522 B1 | 11/2001 | Zimmon |
| 6,403,035 B1 | 6/2002 | Caratsch et al. |
| 6,485,436 B1 | 11/2002 | Truckai et al. |
| 6,535,284 B1 | 3/2003 | Hajduk et al. |
| 6,646,721 B2 | 11/2003 | Compter |
| 6,899,850 B2 | 5/2005 | Haywood |
| 7,166,113 B2 | 1/2007 | Arambula |
| 7,175,612 B2 | 2/2007 | Felix et al. |
| 7,397,894 B2 | 7/2008 | Nakai |
| 7,546,925 B1 | 6/2009 | Zuk, Jr. |
| 7,662,109 B2 | 2/2010 | Hibner |
| 7,692,144 B2 | 4/2010 | Watanabe |
| 7,715,523 B2 | 5/2010 | Lafferty |
| 7,753,857 B2 | 7/2010 | Hibner |
| 7,758,601 B2 | 7/2010 | Heywang-Koebrunner et al. |
| 7,856,081 B2 | 12/2010 | Peschmann |
| 7,858,038 B2 | 12/2010 | Andreyko et al. |
| 7,867,173 B2 | 1/2011 | Hibner et al. |
| 7,972,062 B2 | 7/2011 | Nicolosi |
| 8,038,347 B2 | 10/2011 | Manak |
| 8,038,627 B2 | 10/2011 | Hibner |
| 8,050,735 B2 | 11/2011 | Feke |
| 8,052,616 B2 | 11/2011 | Andrisek et al. |
| 8,162,140 B2 | 4/2012 | Hansen |
| 8,177,728 B2 | 5/2012 | Hibner et al. |
| 8,213,570 B2 | 7/2012 | Panesar |
| 8,235,913 B2 | 8/2012 | Hibner et al. |
| 8,284,896 B2 | 10/2012 | Singh |
| 8,702,623 B2 | 4/2014 | Parihar |
| 8,741,232 B2 | 6/2014 | Baysal |
| 8,764,679 B2 | 7/2014 | Miller et al. |
| 8,911,381 B2 | 12/2014 | Hibner et al. |
| 8,923,603 B2 | 12/2014 | Weston |
| 8,956,306 B2 | 2/2015 | Hibner |
| 8,971,484 B2 | 3/2015 | Beckmann |
| 8,983,030 B2 | 3/2015 | Ookawa |
| 9,068,920 B2 | 6/2015 | Churilla |
| 9,129,715 B2 | 9/2015 | Adler |
| 9,188,696 B2 | 11/2015 | Schafer |
| 9,234,855 B2 | 1/2016 | Watanabe |
| 9,277,895 B2 | 3/2016 | Hara |
| 9,322,790 B2 | 4/2016 | Ookawa |
| 9,326,755 B2 | 5/2016 | Fiebig |
| 9,329,139 B2 | 5/2016 | Itou |
| 9,341,546 B2 | 5/2016 | Stuke |
| 9,347,894 B2 | 5/2016 | Sims |
| 9,492,130 B2 | 11/2016 | Flagle et al. |
| 9,557,281 B2 | 1/2017 | Badawi et al. |
| 9,642,581 B2 | 5/2017 | Lowe |
| 9,733,167 B2 | 8/2017 | Wismueller |
| 9,865,424 B2 | 1/2018 | Ikeda |
| 9,943,850 B2 | 4/2018 | Purdy |
| 9,953,799 B2 | 4/2018 | Hakoda |
| 10,008,298 B2 | 6/2018 | King |
| 10,010,296 B2 | 7/2018 | Basu |
| 10,078,093 B2 | 7/2018 | Flagle |
| 10,098,216 B2 | 10/2018 | Kabumoto |
| 10,105,709 B2 | 10/2018 | Purdy |
| 10,145,806 B2 | 12/2018 | Tanaka |
| 10,190,997 B2 | 1/2019 | Aoki |
| 10,201,331 B2 | 2/2019 | Fleming |
| 10,322,412 B2 | 6/2019 | Purdy |
| 10,393,678 B2 | 8/2019 | Watanabe |
| 10,488,351 B2 | 11/2019 | Butani |
| 10,705,030 B2 | 7/2020 | Watanabe |
| 10,753,836 B2 | 8/2020 | O'Driscoll |
| 10,809,208 B2 | 10/2020 | Yashima |
| 11,083,426 B2 | 8/2021 | DeFreitas |
| 11,246,551 B2 | 2/2022 | Butani |
| 11,317,881 B2 | 5/2022 | Purdy |
| 11,358,149 B2 | 6/2022 | Purdy |
| 2002/0007188 A1 | 1/2002 | Arambula |
| 2002/0145722 A1 | 10/2002 | Compter |
| 2002/0193656 A1 | 12/2002 | Ravins et al. |
| 2003/0087423 A1 | 5/2003 | Haywood |
| 2003/0216730 A1 | 11/2003 | Barry et al. |
| 2004/0022350 A1 | 2/2004 | Gregerson et al. |
| 2004/0174031 A1 | 9/2004 | Rasmussen |
| 2004/0218716 A1 | 11/2004 | Freifeld |
| 2005/0051723 A1 | 3/2005 | Neagle et al. |
| 2005/0065453 A1 | 3/2005 | Shabaz et al. |
| 2005/0112034 A1 | 5/2005 | McCormick |
| 2005/0124913 A1 | 6/2005 | Damarati |
| 2005/0148842 A1 | 7/2005 | Wang |
| 2006/0074343 A1 | 4/2006 | Hibner |
| 2006/0116603 A1 | 6/2006 | Shibazaki et al. |
| 2006/0173266 A1 | 8/2006 | Pawluczyk et al. |
| 2007/0106176 A1 | 5/2007 | Mark et al. |
| 2007/0116612 A1 | 5/2007 | Williamson |
| 2007/0166834 A1 | 7/2007 | Williamson, IV et al. |
| 2007/0237684 A1 | 10/2007 | Hansen |
| 2007/0239067 A1 | 10/2007 | Hibner et al. |
| 2007/0270714 A1 | 11/2007 | Cushner et al. |
| 2008/0004545 A1 | 1/2008 | Garrison |
| 2008/0082021 A1 | 4/2008 | Ichikawa |
| 2008/0132805 A1 | 6/2008 | Heywang-Koebrunner et al. |
| 2008/0214955 A1 | 9/2008 | Speeg et al. |
| 2008/0221480 A1 | 9/2008 | Hibner et al. |
| 2008/0228103 A1 | 9/2008 | Ritchie et al. |
| 2008/0249434 A1 | 10/2008 | Hashimshony et al. |
| 2009/0088663 A1 | 4/2009 | Miller et al. |
| 2009/0088666 A1 | 4/2009 | Miller et al. |
| 2009/0131818 A1 | 5/2009 | Speeg et al. |
| 2009/0131820 A1 | 5/2009 | Speeg |
| 2009/0131823 A1 | 5/2009 | Andreyko et al. |
| 2009/0171243 A1 | 7/2009 | Hibner et al. |
| 2009/0171244 A1 | 7/2009 | Ning |
| 2009/0213987 A1 | 8/2009 | Stein |
| 2010/0081964 A1 | 4/2010 | Mark |
| 2010/0152611 A1 | 6/2010 | Parihar |
| 2010/0160824 A1 | 6/2010 | Parihar |
| 2010/0160826 A1 | 6/2010 | Parihar |
| 2010/0191145 A1 | 7/2010 | Lafferty |
| 2010/0317997 A1 | 12/2010 | Hibner |
| 2011/0285837 A1 | 11/2011 | Bello |
| 2012/0051514 A1 | 3/2012 | Sims et al. |
| 2012/0053484 A1 | 3/2012 | Parks |
| 2012/0116246 A1 | 5/2012 | Hibner |
| 2012/0123295 A1 | 5/2012 | Sanbuichi |
| 2012/0245485 A1 | 9/2012 | Hibner |
| 2013/0053724 A1 | 2/2013 | Fiebig |
| 2013/0231585 A1 | 9/2013 | Flagle |
| 2014/0039343 A1 | 2/2014 | Mescher |
| 2014/0051986 A1 | 2/2014 | Zhao et al. |
| 2014/0065656 A1 | 3/2014 | Baysal |
| 2014/0072104 A1 | 3/2014 | Jacobsen et al. |
| 2014/0198893 A1* | 7/2014 | Badawi .............. G01N 23/046 |
| | | 378/19 |
| 2014/0257135 A1 | 9/2014 | DeFreitas |
| 2014/0276209 A1 | 9/2014 | Hibner |
| 2015/0083893 A1 | 3/2015 | Wismueller |
| 2015/0131773 A1 | 5/2015 | Lowe et al. |

(56) References Cited

U.S. PATENT DOCUMENTS

| | | |
|---|---|---|
| 2015/0209017 A1 | 7/2015 | Fleming |
| 2017/0131311 A1 | 5/2017 | Flagle |
| 2017/0336706 A1 | 11/2017 | Wang |
| 2019/0054217 A1 | 2/2019 | Axon |
| 2019/0072463 A1 | 3/2019 | O'Driscoll |
| 2019/0167869 A1 | 6/2019 | Willard |
| 2019/0285558 A1 | 9/2019 | DeFreitas |
| 2019/0346471 A1 | 11/2019 | Flagle |
| 2020/0061622 A1 | 2/2020 | Purdy |
| 2020/0187923 A1 | 6/2020 | Safir |
| 2020/0268331 A1 | 8/2020 | Purdy |
| 2020/0386657 A1 | 12/2020 | O'Driscoll |
| 2022/0039766 A1 | 2/2022 | DeFreitas |
| 2022/0110597 A1 | 4/2022 | Chen |
| 2022/0331808 A1 | 10/2022 | Purdy |
| 2023/0012310 A1 | 1/2023 | Stango |
| 2023/0014922 A1 | 1/2023 | DeFreitas |
| 2023/0136395 A1 | 5/2023 | Chen et al. |

FOREIGN PATENT DOCUMENTS

| | | |
|---|---|---|
| JP | 2014-526937 | 10/2014 |
| JP | 2015-520402 | 7/2015 |
| JP | 2016-154878 | 9/2016 |
| WO | 8101363 | 5/1981 |
| WO | 2008/025146 | 3/2006 |
| WO | 2007021905 | 2/2007 |
| WO | 2009/120206 | 10/2009 |
| WO | 2011/140374 | 11/2011 |
| WO | 2012/074885 | 6/2012 |
| WO | 2013/166497 | 11/2013 |
| WO | 2018/204710 | 11/2018 |
| WO | 2019/216766 | 11/2019 |

OTHER PUBLICATIONS

PCT International Preliminary Report on Patentability in International Application PCT/US2018/050490, dated Mar. 26, 2020, 31 pages.

PCT International Search Report and Written Opinion in International Application PCT/US2018/050490, dated Dec. 27, 2018, 34 pages.

Watanabe, M. et al., "The quantitative analysis of thin specimens: a review of progress from the Cliff-Lorimer to the new zeta-factor methods", Journal of Microscopy, vol. 221, No. 2, Feb. 1, 2006, p. 91.

* cited by examiner

IMAGING SYSTEM WITH ADAPTIVE OBJECT MAGNIFICATION

CROSS REFERENCE TO RELATED APPLICATIONS

This application is a continuation of U.S. patent application Ser. No. 16/646,379, filed Mar. 11, 2020, now U.S. Pat. No. 11,317,881, which is a National Stage Application of PCT/US2018/050490, filed Sep. 11, 2018, which claims of U.S. Provisional Application No. 62/556,566, entitled "IMAGING SYSTEM WITH ADAPTIVE OBJECT MAGNIFICATION," filed on Sep. 11, 2017, the entireties of which are incorporated herein by reference as if set forth in full. To the extend appropriate, a claim of priority is made to each of the above disclosed applications.

FIELD OF THE INVENTION

This invention generally relates to the imaging of objects and, more particularly, to devices and methods for obtaining both two and three-dimensional images of objects for use in inspection and analysis of the objects.

BACKGROUND OF THE INVENTION

There are currently numerous non-invasive imaging techniques that can be used to produce images of a given object for use in inspection, analysis, and the like. Such techniques include X-rays, magnetic resonance imaging ("Mill"), computed tomography ("CT" or "microtomography") scans, ultrasound and optical imaging using structured light, among others.

As an example, definitive diagnosis of cancers such as breast cancer is typically accomplished through the surgical removal (e.g., biopsy) of the suspicious tissue (e.g., lesion) by a surgeon for further examination by a radiologist and/or pathologist. After a surgeon has appropriately identified a location of a possible lesion, the surgeon proceeds to excise tissue (e.g., object) that includes the lesion and then verify that the entirety of the suspicious area is within the margins of the excised tissue. In this regard, a radiologist or the like will often x-ray or otherwise image the excised tissue specimen from multiple views (e.g., orthogonal views) to confirm appropriate tissue margins. Once the tissue margins have been confirmed, the surgeon may then appropriately mark or otherwise indicate where on the excised tissue specimen a pathologist should focus during subsequent analysis and diagnosis.

In the event that the area of interest is too close or even contacts the tissue margins, the surgeon may need to excise additional tissue. Accordingly, it is important for the radiologist and surgeon to have confidence from the various images of the tissue specimen that the tissue margins are sufficient and that all potentially cancerous or worrisome tissue is fully contained within the specimen to limit the number of further tissue excisions.

As another example, objects such as printed circuit boards and other electrical devices are known to include a substrate with numerous tiny external electrical bonds whereby an electrical lead is soldered to the device. Because these kind of bonds are often on the order of a few microns in diameters, they typically cannot be visually inspected with the naked eye and thus must be magnified in some manner to inspect the bonds and other components for flaws and the like. Manufacturers thus often x-ray such electrical devices to identify any internal defects in the devices as part of nondestructive testing (NDT) of the devices.

SUMMARY

Disclosed herein is a cabinet imaging system that can automatically obtain and provide two and three-dimensional digital images of various types of objects (e.g., tissue specimens, animals, electrical devices, etc.) for use in analysis thereof in a manner free of manual repositioning of the objects as well as free of movement of an electromagnetic radiation source and detector within or relative to the housing of the cabinet. While much of this disclosure will be in the context of objects such as a tissue specimens, it is to be understood that the disclosed cabinet imaging system and related methods can be used to obtain orthogonal and reconstructed three-dimensional images of objects in various other contexts such as medical (e.g., small animals), manufacturing (e.g., electrical devices), research, security, defense, and the like.

In one aspect, a cabinet for use in obtaining images of an object includes a housing having a plurality of walls that surround an interior chamber, an imaging detector positioned relative to the housing, a source of electromagnetic radiation (e.g., x-ray tube or the like) positioned relative to the housing and that is configured to emit a beam of electromagnetic radiation along a first axis towards the imaging detector, an object receiving surface disposed within the interior chamber for receiving an object thereon, and a motion control mechanism for moving the object receiving surface along a second axis relative to the source and the first axis, where the first and second axes are non-parallel and non-perpendicular.

For instance, the motion control mechanism may include a first linear drive that is configured to move the object receiving surface along the second axis. The first linear drive may include a sliding member that is configured to slide along the second axis, and where the object receiving surface is interconnected to the sliding member. The motion control mechanism may also include a rotary drive that is interconnected to the object receiving surface and the sliding member of the first linear drive, where the rotary drive is configured to rotate the object receiving surface about a rotational axis that is perpendicular to the first axis.

In one arrangement, the housing may include a false floor within the interior chamber that divides the interior chamber into a first chamber and a second chamber, where the object receiving surface is disposed within the first chamber. For instance, at least a portion of the motion control mechanism may be disposed in the second chamber and/or in the first chamber.

In another aspect, a method for use in imaging an object in a cabinet includes operating a motion control apparatus in a cabinet to move an object within the cabinet along a first axis relative to a source of electromagnetic radiation and an imaging detector from a first position on the first axis to a second position on the first axis, and triggering the source to emit a beam of electromagnetic radiation along a second axis through the object in its second position towards the detector, where the first and second axes are non-parallel and non-perpendicular.

Various refinements may exist of the features noted in relation to the various aspects. Further features may also be incorporated in the various aspects. These refinements and additional features may exist individually or in any combination, and various features of the aspects may be combined. In addition to the exemplary aspects and embodiments described above, further aspects and embodiments will become apparent by reference to the drawings and by study of the following descriptions.

BRIEF DESCRIPTION OF THE DRAWINGS

For a more complete understanding of the present invention and further advantages thereof, reference is now made to the following Detailed Description, taken in conjunction with the drawings, in which.

DETAILED DESCRIPTION

Figure 1:
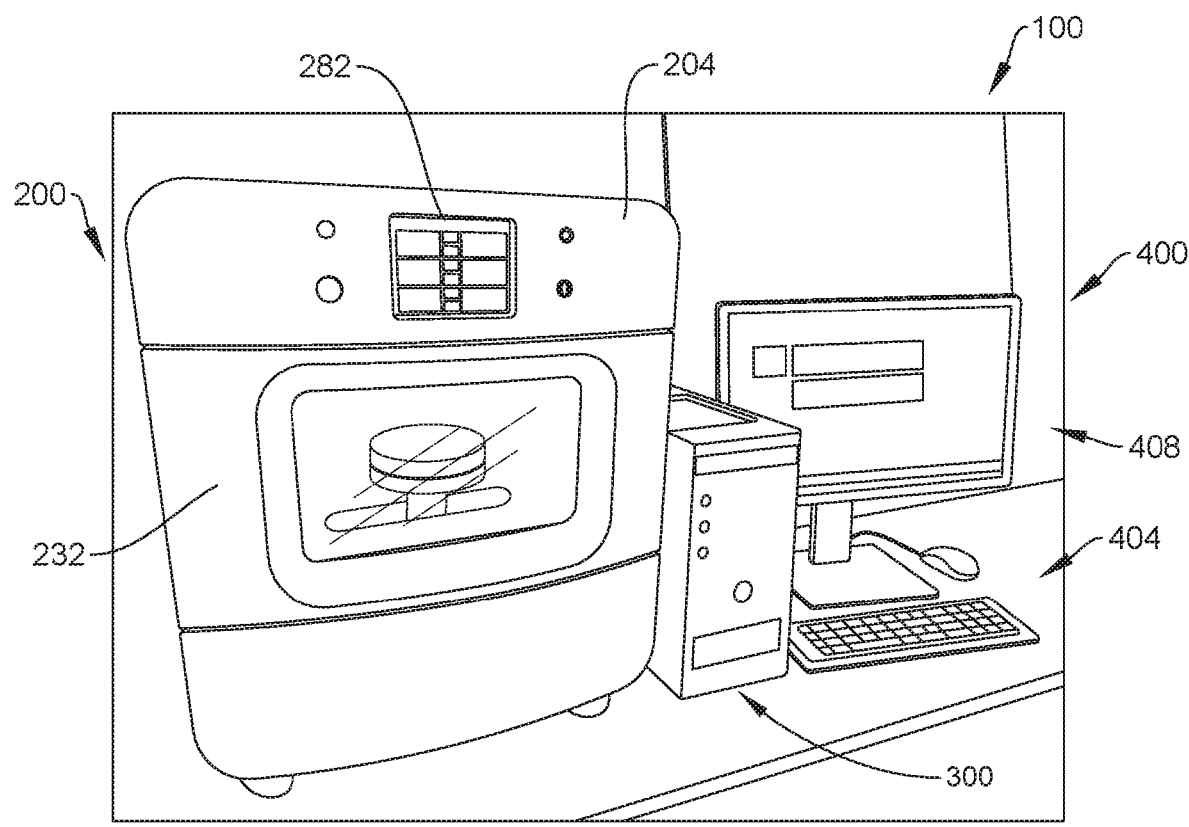
FIG. 1 is a perspective view of an imaging system that is configured to automatically obtain and provide two and three-dimensional digital images of objects, according to one embodiment.

Reference will now be made to the accompanying drawings, which assist in illustrating the various pertinent features of the various novel aspects of the present disclosure. In this regard, the following description is presented for purposes of illustration and description. Furthermore, the description is not intended to limit the inventive aspects to the forms disclosed herein. Consequently, variations and modifications commensurate with the following teachings, and skill and knowledge of the relevant art, are within the scope of the present inventive aspects.

With initial respect to FIGS. 1-4, an imaging system 100 that is configured to automatically obtain and provide two dimensional (e.g., orthogonal) digital images and three-dimensional (e.g., reconstructed) digital images of various types of objects, according to one embodiment, is illustrated. For instance, the disclosed system 100 allows for tissue margin verification to be obtained in the surgery room, thus enabling cases to be completed faster, limiting the time patients need to be under examination, and limiting patient recalls. The disclosed system also can automatically obtain such images substantially free of manual repositioning of the object between images and free of movement of the source of electromagnetic radiation (e.g., x-ray source) or the imaging detector (e.g., x-ray detector), thus reducing the number of moving parts in the system and allowing for the provision of a smaller imaging cabinet. As noted previously, the disclosed system 100 can also be used in various other contexts such as other types of medical (e.g., small animals), manufacturing (e.g., electrical devices), research, security, defense, and the like.

The system 100 generally includes a shielded imaging cabinet 200, a computing system 300 (e.g., service, desktop computer, etc., including processor(s), memory, etc.), and one or more peripherals 400 electrically interconnected to the computing system 300 such as input devices 404 (e.g., keyboard, mouse), output devices 408 (e.g., monitor), and the like. The computing system 300 may generally be configured to receive input from a technician, physician, or the like regarding an object to be imaged (e.g., patient information, object information, etc.) and store the same, initiate an imaging procedure based at least in part on the received input (e.g., trigger an x-ray source to emit x-rays through the object for receipt at an x-ray detector), move an object imaging platform on which the object is disposed into one or more various positions within the cabinet 200 as discussed more fully below), receive and process signals from the x-ray detector, and generate various 2D and 3D images of the object for presentation to the physician or the like (e.g., on output device/monitor 408) for use in tissue margin verification. The computing system 300 may allow the physician or the like to view the 2D and 3D images on a screen and slice through the 3D image at almost any position to see internal details of the same.

While the computing system 300 is illustrated as being separate from the cabinet 200, the computing system 300 may in other arrangements be appropriately combined with the cabinet 200 into a single unit. In other arrangements, the computing system 300 may be disposed remote from the cabinet 200 such as in a separate room or even geographically remote and in communication therewith by one or more networks (e.g., LAN, WAN, Internet) or may be distributed among a plurality of computing systems (e.g., servers, networks, etc.). In any case, all references to "computing system" or similar herein are intended to encompass one or processors or processor cores that are configured to execute one or more sets of computer-readable instruction sets to carry out the various determinations and functionalities disclosed herein (e.g., determining a position of a object within the interior chamber 208 of the cabinet 200, triggering motion control apparatus 500 to move the object within the cabinet based on the determined position, triggering electromagnetic radiation source 220 to emit one or more electromagnetic radiation beams 222 through object, generating image data sets based on electromagnetic radiation beams received at detector 224, and the like, discussed herein).

Broadly, the cabinet 200 includes a housing 204 that generally defines an interior chamber 208 for receiving an object (e.g., tissue specimen) on an object receiving surface 216 of an object holder 212 (e.g., platform, table, stage, etc.) that is movable within the interior chamber 208 relative to a source 220 of electromagnetic radiation (e.g., beam 222) and an imaging detector 224. The imaging detector 224 is configured to receive electromagnetic radiation emitted from the source 220 after passing through an object (not shown) received on the object receiving surface 216. In one arrangement, the object holder 212 may include one or more walls that extend upwardly away from the object receiving surface 216 to form a container for the object. The object holder 212 may be constructed from any appropriate radiolucent or low radio-density material (e.g., as one example, polymeric foam) to substantially eliminate or at least reduce attenuation of beam of electromagnetic radiation passing through the object holder 212; this arrangement thus substantially eliminates or at least reduces the likelihood of the object holder 212 appearing in an image of the object and correspondingly increases the quality (e.g., contrast, resolution, etc.) of the image (e.g., for use in verifying tissue margins, identifying suspicious locations or areas in the excised tissue specimen to be subsequently analyzed by a pathologist, and/or the like).

Figure 2A:
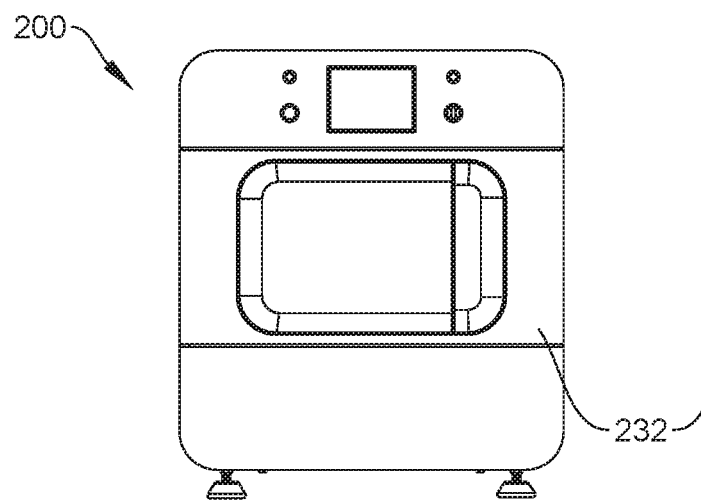
FIGS. 2a-2b are front and side views of an imaging cabinet of the system of FIG. 1.
Figure 2B:
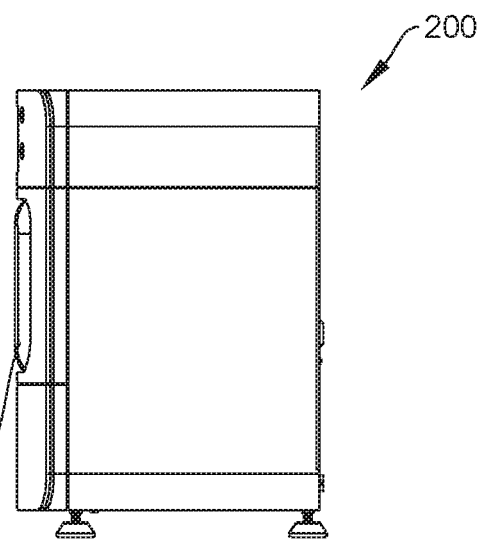

The housing 204 may generally include any appropriate arrangement of walls 228, electromagnetic shielding (e.g., lead sheets, etc.), brackets, and other componentry (not all shown in the interest of clarity) to define the interior chamber 208, limit electromagnetic radiation from escaping or leaking from the housing 204, and non-movably secure the source 220 and detector 224 relative to the housing 204 (i.e., the source 220 and detector 224 are non-movable relative to the walls 228, brackets, etc. of the housing 204 during imaging procedures). Furthermore, the housing 204 includes a shielded access member 232 (e.g., door) that is movable between an open position (as shown in FIG. 3) and a closed position (as shown in FIGS. 1 and 2a) to provide access to the interior chamber 208 so as to place objects therein and remove objects therefrom.

Figure 3:
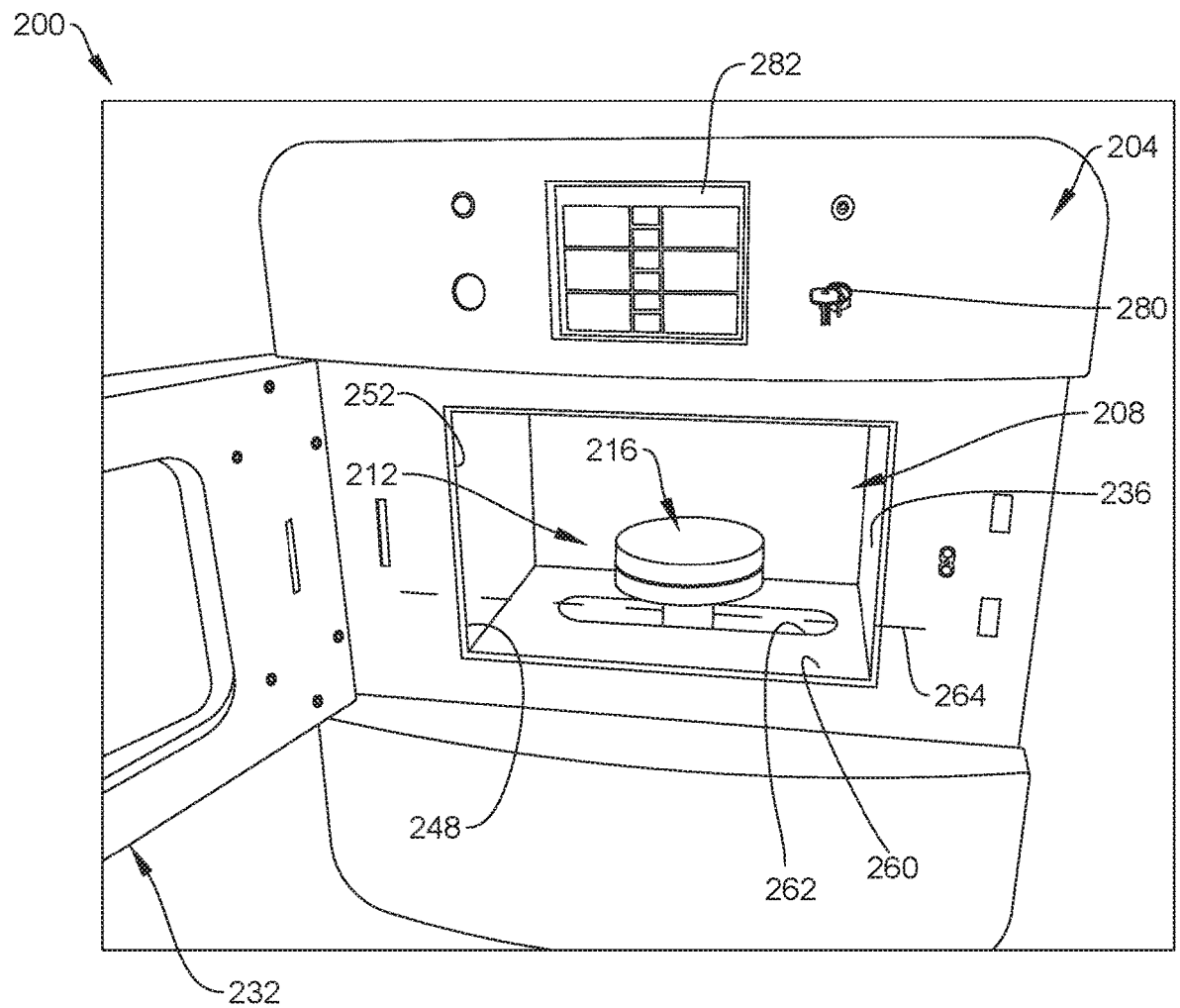
FIG. 3 is a perspective view of the imaging cabinet of FIGS. 2a-2b with a door of the cabinet in an open position and exposing an interior chamber of the cabinet.
Figure 4:
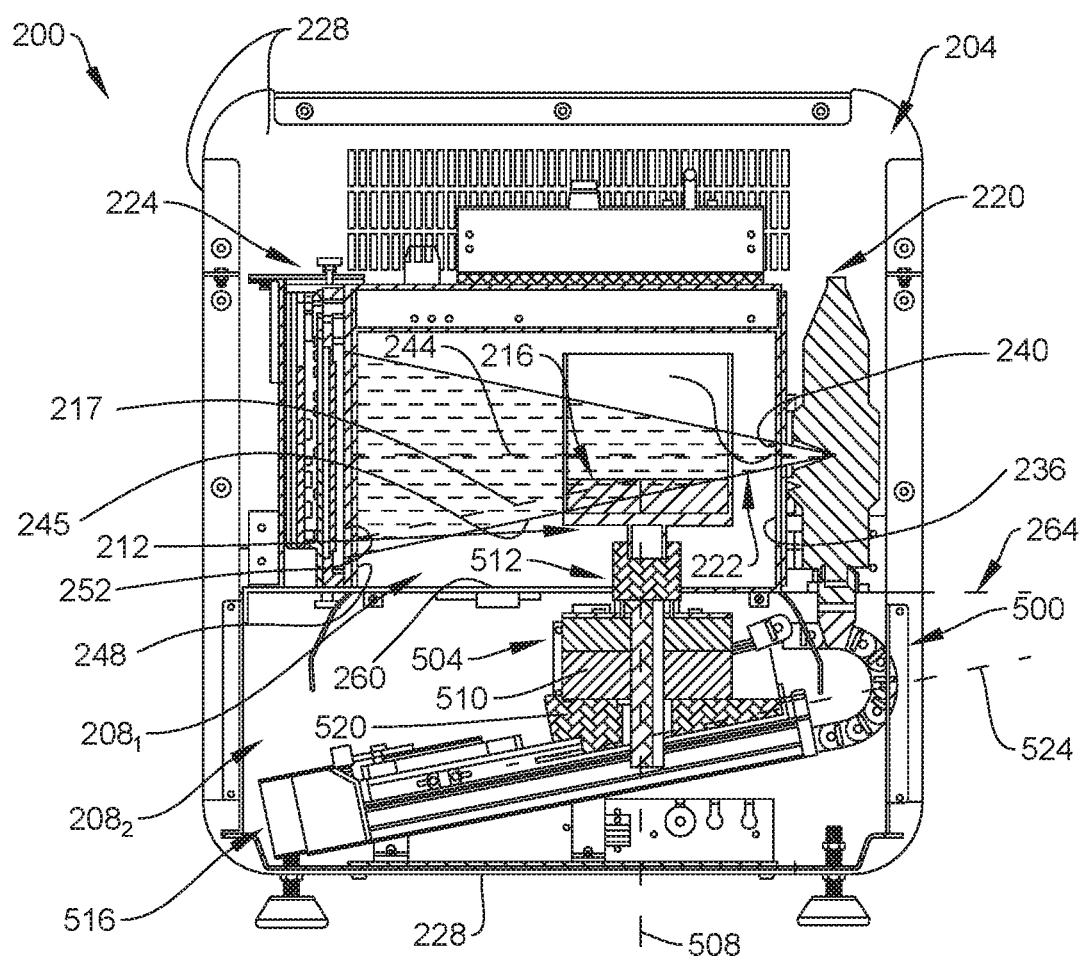
FIG. 4 is a sectional view through the imaging cabinet of FIGS. 2a-2b.

With reference now to FIGS. 3-4, the source 220 may be rigidly fixed relative to a first sidewall or portion 236 of the housing 204 in any appropriate manner such that electromagnetic radiation beams 222 (e.g., x-ray cone beam) emitted from the source 220 may pass through an opening or aperture 240 in the first side portion 236 along an axis 244 (e.g., a central axis) towards the detector 224. The detector 224 may be rigidly fixed relative to an opposite second sidewall or portion 248 of the housing 204 in any appropriate manner such that the electromagnetic radiation beams 222 emitted along the axis 244 may be received through an opening or aperture 252 in the second side portion 248 at the detector 224. Each of the source 220 and the detector 224 may be appropriately electrically interconnected to the computing system 300 so as to be appropriately controlled by one or more controllers or processors (e.g., executing any appropriate computer-readable instructions or logic as stored on any appropriate memory structure) during imaging procedures as described herein (e.g., see FIG. 10, discussed below).

In the context of cancer diagnosis and the like, it is important for an excised tissue specimen to remain in a substantially constant shape and/or a substantially undisturbed position with respect to some particular reference point or device (e.g., relative to a tray or carrier used to transport the specimen) between excision up to and including pathologist diagnosis. For instance, reshaping of the tissue specimen (e.g., compressing, folding, etc.) between the taking of first and second orthogonal images (e.g., for use in tissue margin detection) through manual repositioning of the specimen by a technician or the like can make accurate tissue margin analysis difficult or even impossible. Furthermore, obtaining three-dimensional images of specimens has become an important technique for use in tissue margin verification which involves obtaining a plurality of images about an outer periphery of the specimen and then reconstructing (e.g., through digital processing) the plurality of images into a three-dimensional data set and a corresponding three-dimensional image which can be manipulated by a technician or the like to analyze the tissue margins. While some existing imaging cabinets include electromagnetic radiation sources and/or detectors that move relative to a specimen that remains stationary within the cabinet for use in obtaining two dimensional orthogonal images and three-dimensional specimen images, such existing cabinets thus require componentry, space, and the like to allow for such moving sources and/or detectors which can result in a larger footprint of the cabinet among other inefficiencies.

In this regard, the cabinet 200 includes a motion control mechanism or apparatus 500 for moving an object received or placed on the object receiving surface 216 relative to the source 220, the detector 224, and the axis 244 along which the beams 222 are emitted from the source 220 to the detector 224. In one embodiment, the motion control mechanism 500 may include a rotary drive 504 that is configured to rotate the object holder 212 (and thus the object receiving surface 216 and an object received thereon) about a rotational axis 508 that is substantially perpendicular to the axis 222 along which the beams 222 travel.

For instance, the rotary drive 504 may include a motor 510 that is configured to rotate a shaft assembly 512 in first and/or second directions about the rotational axis 508 under control of the computing system 300. The shaft assembly 512 may be rigidly or non-movably attached to the object holder 212 in any appropriate manner such that rotation of the shaft assembly 512 induces simultaneous corresponding rotation of the object holder 212 (and thus the object receiving surface 216 and the object placed thereon) about the rotational axis 508.

In operation, and after an object has been placed on the object receiving surface 212, the computing system 300 may trigger the source 220 to emit a beam 222 of electromagnetic radiation along the axis 244 through the object for receipt at the detector 224, whereupon the received electromagnetic radiation signals may be appropriately processed by the computing system 300 or the like for generate of an image of the object with the object in a first rotational position. As discussed above, orthogonal and/or three-dimensional imaging of the object may be used to verify tissue margins in the case of tissue specimens, detect defects in the case of electrical devices, and the like. In this regard, the computing system 300 may trigger the motion control apparatus 500 to rotate the object receiving surface 212 and object by 90° about the rotational axis 508 from the first rotational position to a second rotational position and then trigger the source 220 to emit a beam 222 of electromagnetic radiation along the axis 244 through the object for receipt at the detector 224 for generation of another (orthogonal) image of the object with the object in the second rotational position.

Additionally or alternatively, the computing system 300 may trigger the motion control apparatus 500 to rotate the object receiving surface 212 and object and simultaneously trigger the source 220 to emit a beam 222 of electromagnetic radiation along the axis 244 through the object as it is rotating about the rotational axis 508. The computing system 300 may be configured to receive and process detected electromagnetic radiation signals from the detector 224 as the object is rotating about the rotational axis 508 to generate a plurality of two dimensional images (e.g., several times per second or more) which may then be reconstructed by the computer device 300 or the like into a three-dimensional data set and a corresponding three-dimensional image of the object. The three-dimensional images can be used in combination with or separate from the two dimensional images as part of tissue margin verification, defect detection, and the like.

In some situations, a maximum outline of the object may not substantially fill the area of the beam (e.g., where the area of the beam extends within a reference plane that is substantially parallel to the first and second side walls 236, 248 of the housing 204 and perpendicular to the beam axis 244) due to the size or dimensions of the object, due to the positioning of the object receiving surface 216 relative to the beam axis 244, and/or the like which may otherwise result in inaccurate or distorted images of the object. In another characterization, a centroid of the object may not substantially intersect the beam axis 244 or the centroid may substantially intersect the beam axis 244 but the object may be positioned too far away from the source 220 to obtain images of an appropriate magnification.

In this regard, the motion control apparatus 500 (under control of the computing system 300) may be configured to linearly move the object receiving surface 212 and object thereon along an axis relative to the source 220, the detector 224, and the beam axis 244 so as to move the centroid of the object into substantial intersection with the beam axis 244 and/or to move the object closer to the source 220 for use in obtaining higher quality images of the object. In one arrangement and as shown in FIG. 4, the motion control apparatus 500 may include at least one linear drive 516 (including a motor or other driving mechanism, not labeled) that is configured to linearly move a sliding member 520 in first and second opposite directions along an axis 524 that is non-parallel and non-perpendicular to the beam axis 244. For instance, the rotary drive 504 (e.g., the motor 510) may be rigidly or non-movably attached to the sliding member 520 in any appropriate manner such that movement of the sliding member 520 along the axis 524 induces corresponding linear movement of the object receiving surface 216 along an axis 217 that is also non-parallel and non-perpendicular to the beam axis 244.

The motor or driving mechanism of the linear drive 516 may be rigidly fixed to the housing 204 (e.g., to the walls 228 or other fixed structures) in any appropriate manner. As shown in FIG. 4, the linear drive 516 may be rigidly fixed within the interior chamber 208 of the housing 204 below or underneath the object holder 212 and object receiving surface 216. In one arrangement, the housing 204 may include a false floor 260 (e.g., panel, sheet, etc.) that is configured to separate or divide the interior chamber 208 into a first interior chamber $208_1$ and a second interior chamber $208_2$. The first interior chamber $208_1$ may be configured to house or contain the object holder 212, object thereon, and beam 222 while the second interior chamber $208_2$ may be configured to house or contain the linear and rotary drives 516, 504. In one arrangement, any electromagnetic radiation shielding included in the housing may only extend about the walls or panels of the first interior chamber $208_1$ (including the false floor 260) so as to contain electromagnetic radiation emitted by the source 220 within the first interior chamber $208_1$ and also reduce the weight of the cabinet 200 and costs for construction thereof by limiting the use of shielding where it does not necessarily need to be used (e.g., about the motion control apparatus 500 in the second interior chamber $208_2$).

To allow the motion control apparatus 500 to be connected to the object holder 212 across the false floor 260, the false floor 260 may include an elongated opening or slot 262 extending along a longitudinal axis 264 that is disposed within a reference plane (not shown) along with the axis 524 of the linear drive 516. In this regard, a portion of the object holder 212 and/or the shaft assembly 512 (as shown, the shaft assembly 512) may be configured to slide within the slot 262 as the motion control apparatus 500 moves the sliding member 520 and thus the object receiving surface 216 and their axes 524, 217 (via the shaft assembly 512).

In the embodiment of FIG. 4, the axis 524 may be configured to generally converge towards the beam axis 244 in a direction from the detector 224 towards the source 220. In one arrangement, the axis 524 (and thus the axis 217) may be substantially parallel to an axis 245 along which an outer periphery of the beam 222 (e.g., as shown, a lower outer periphery) extends from the source 220 to the detector 224 (e.g., in the case of a cone beam 222). Stated differently, the axis 245 may form an angle α with the beam axis 244, and the axis 524 may form the same angle α with the beam axis 244.

Figure 9:
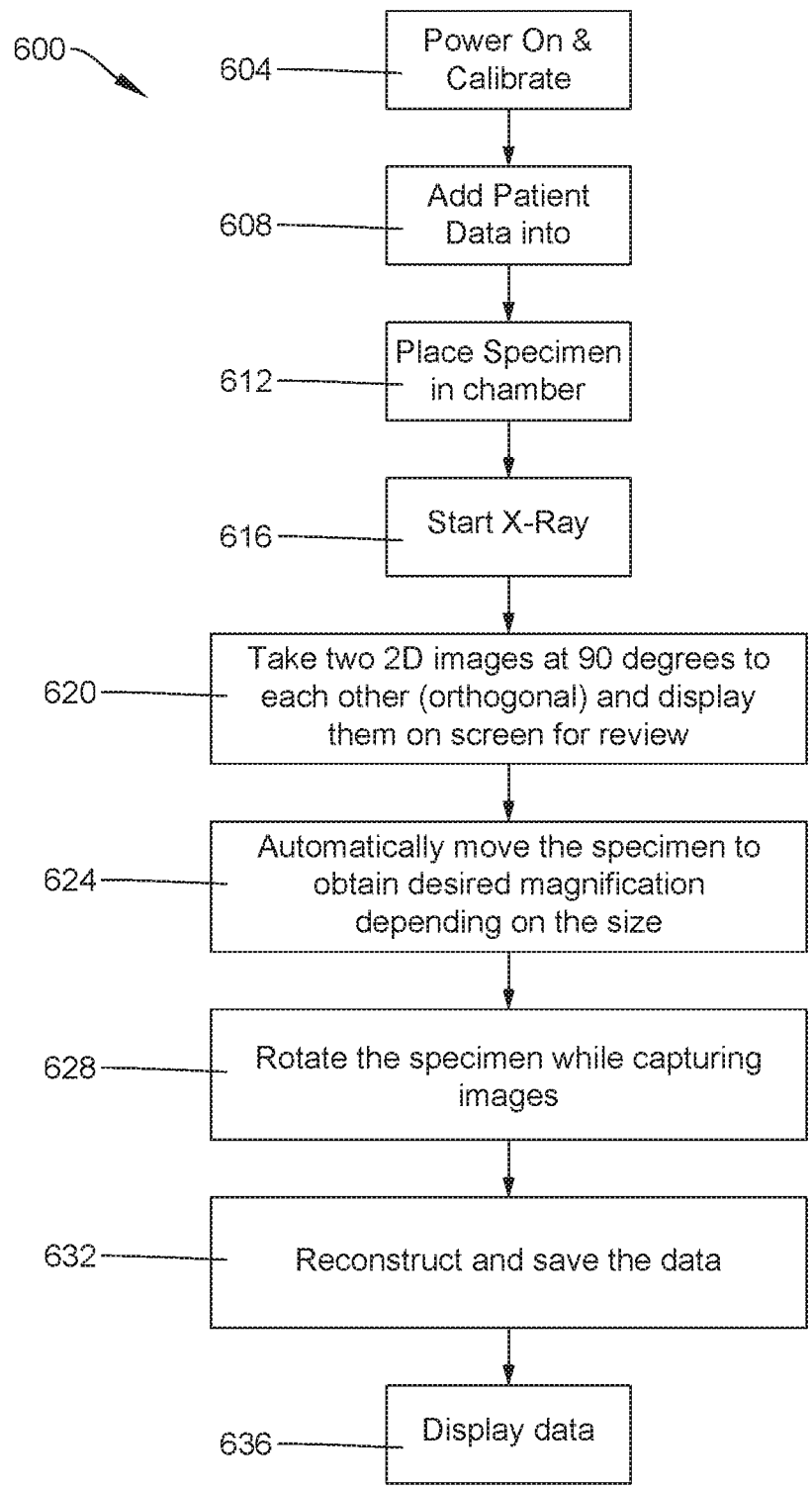
FIG. 9 is a flow diagram of a method of obtaining images of an object.

To more fully understand the various functionalities of the disclosed system, additional reference will now be made to FIG. 9 which presents a flow diagram of a method 600 of obtaining images of an object in addition to FIGS. 5a, 5b, 6a, and 6b which present partial side and perspective views of an object O being moved by the motion control apparatus 500 (not illustrated in FIGS. 5a, 5b, 6a, and 6b) as part of an imaging procedure. While certain steps are shown in a particular order in FIG. 9, it is to be understood that more or fewer steps may be included in the same or different order than shown in FIG. 9.

The system 100 may initially be powered on and calibrated 604 and appropriate object information (e.g., patient name and ID number, body portion from where specimen excised, part number, etc.) may be inputted 608 into the cabinet 200 and/or computing system 300 in any appropriate manner. For instance, a power switch 280 may be manipulated by a user into an "on" position and a screen 282 on the cabinet (or in other location) may provide a status of the cabinet 200 (e.g., calibrating, ready, in use, etc.). Also for example, one or more of the input devices 404 may be manipulated to input patient information regarding the imaging procedure into the computing system 300 which may be displayed on the output device 408 in any appropriate manner.

The object O may eventually be placed 612 into the interior chamber 228 (e.g., the first interior chamber $228_1$). For instance, the access member 232 may be opened into the position shown in FIG. 3, the object O placed onto the object receiving surface 216 of the object holder 212, and the access member 232 closed into the position shown in FIG. 1. Also see FIGS. 5a-5b. This position of the object O in the interior chamber 228 may be considered a first position of the object O on an axis 290 that is parallel to the axis 217 along which the object receiving surface 216 travels (and thus a first position of the object receiving surface 216 along the axis 217).

In one arrangement, the method 600 may include starting 616 the imaging procedure and proceeding to take 620 orthogonal images of the object O and present the same on the output device/monitor 408 for review. For instance, after the system has been calibrated and the object O placed into the interior chamber 228, the technician may initiate the orthogonal imaging by way of using the input device(s) 404 in any appropriate manner to trigger the computing system 300 to conduct the orthogonal imaging. Specifically, the computing system 300 may trigger the source 220 to emit a beam 222 of electromagnetic radiation along axis 244 through the object O with the object in a first rotational position so as to be received at the detector 224, whereupon the computing system 300 may appropriately process the signals received from the detector 224 to generate a first orthogonal image of the object O. The corresponding data may be saved in any appropriate manner and the image may be displayed on output device 408 and/or another output device. In the case where the beam 222 is a cone beam or the like as illustrated in FIGS. 5a-5b, the beam 222 may still travel through all or a substantial entirety of the object O even though the centroid C of the object O may not substantially intersect the beam axis 244 (e.g., due to the size or dimensions of the object O or positioning of the object receiving surface 216 relative to the axis 244).

After the first orthogonal image has been obtained, the computing system 300 or the like may trigger the motion control mechanism 500 (e.g., the rotary drive 504) to rotate the object holder 212 (and thus the object receiving surface 216 and object O) by 90° about rotational axis 508 from a first rotational position to a second rotational position. The computing system 300 may then trigger the source 220 to emit a beam 222 of electromagnetic radiation along axis 244 through the object O with the object O in the second rotational position so as to be received at the detector 224, whereupon the computing system 300 may appropriately process the signals received from the detector 224 to generate a second orthogonal image of the object O. Again, the corresponding data may be saved in any appropriate manner (e.g., in storage 312 of FIG. 10, discussed below) and the image may be displayed on output device 408 and/or another output device.

As discussed previously, an increase in the distance between the centroid (e.g., geometrical center) of an object and the beam axis 244 can sometimes result in an increase in the level of distortion in generated images of the object (e.g., in the case of three-dimensional imaging of the object). Furthermore, when the maximum outline of an object fails to substantially fill or encompass a substantial entirety of the area of the beam 222 (e.g., where the area of the beam extends within a reference plane that is substantially parallel to the first and second side walls 236, 248 of the housing 204 and perpendicular to the beam axis 244), the object may be positioned at a less than optimal magnification point within the interior chamber 208 relative to the source 220.

Figure 5:
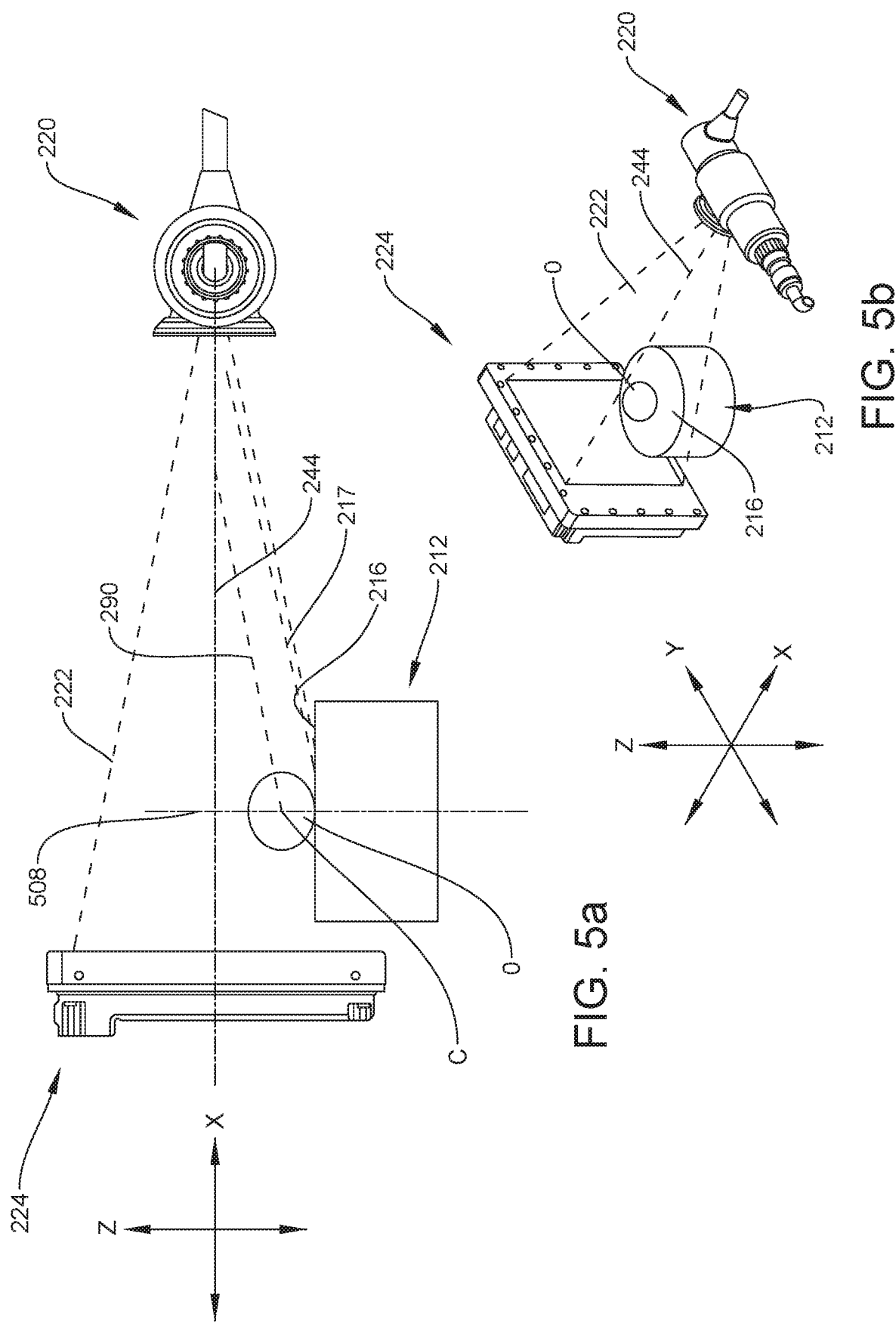
FIGS. 5a-5b and 6a-6b illustrate partial side and perspective views illustrating an object receiving surface with a object thereon moving from a first position to a second position relative to a source of electromagnetic radiation and an imaging detector, according to one embodiment.
Figure 6:
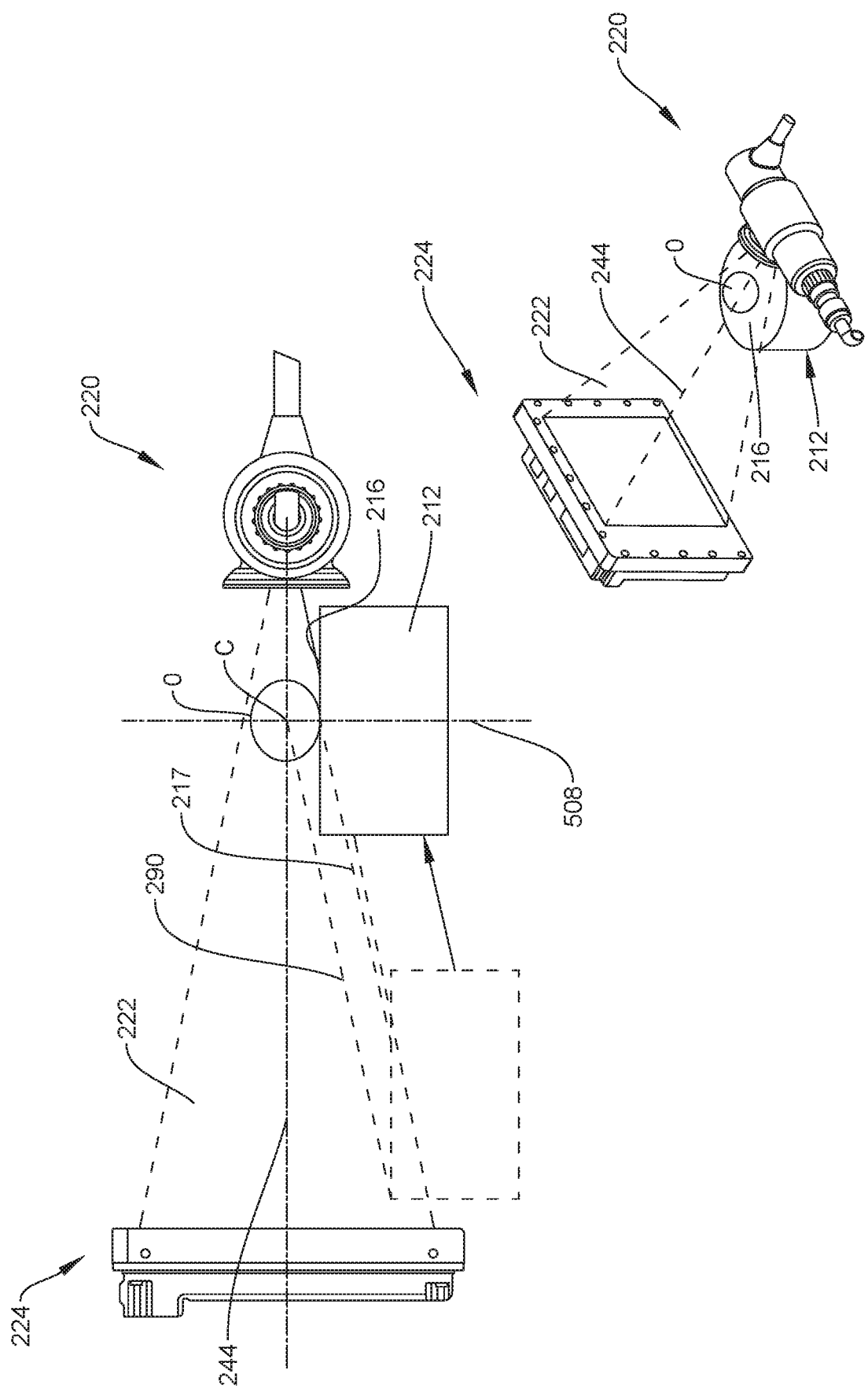

For instance, FIGS. 5a-5b illustrate an object O and the object receiving surface 216 being at first positions along their respective axes 290, 217 (where the axes 290, 217 are parallel to the axis 524 of the linear drive 516 in FIG. 4). In this example, the centroid C of the object O does not substantially intersect the beam axis 244 and the maximum outline of the object O (e.g., maximum outer diameter or dimensions in x, y, and z dimensions) does not substantially fill the area of the beam 222.

Accordingly, the method 600 may include determining a position of the object O relative to the source 220 and the beam axis 244 (e.g., how far the centroid C is from the beam axis 244 and the source 220) and then automatically triggering the motion control apparatus 500, based on the determined position, to move 624 the object O from a first position to a second position whereby its centroid C is closer to or intersects the beam axis 244 and/or so that the centroid C is closer to the source 220. In another characterization, the method 600 may include moving 624 the object O so that its maximum outline more fully fills the area of the beam 222 (e.g., consumes more of the area of the beam 222). For instance, and after determining the relative position of the object O relative to the beam axis 244 and/or the source 220, the computing system 300 may trigger the linear drive 516 (see FIG. 4) to move the sliding member 520 along the axis 524 and thus the object O along axis 290 from the first position illustrated in FIGS. 5a-5b to the second position illustrated in FIGS. 6a-6b whereby the centroid C is closer to or intersects the beam axis 244 and the maximum outline of the object O more fully fills the area of the beam 222.

In one arrangement, and with the object O in a first or initial position such as in FIGS. 5a-5b, the computing system 300 may trigger the source 220 to emit one or more beams of electromagnetic radiation at varying angle offsets through the object O for receipt at the detector 224 and then use signals received from the detector 224 to determine the maximum outline of the object O within the interior chamber 208 relative to the area of the one or more beams (e.g., via any appropriate signal processing logic or the like). The computing system 300 may then appropriately analyze the maximum outline of the object along with a known distance from the source 220 to the isometric center of the object receiving surface 216 to determine an "optimal" magnification of the object O. As just one example, the first position of the object O illustrated in FIGS. 5a-5b may result in a 1.2× magnification of the object O upon beams 222 being emitted along axis 244 and the computing system 300 may determine that a 3.5× magnification of the object O is a more optimal magnification. Accordingly, the computing system 300 may utilize the optimal magnification of the object O along with known parameters of the motion control apparatus 500 (e.g., of the linear drive 516, such as the angle of the axis 524 relative to the beam axis 244) and geometry of the cabinet 200 to trigger the linear drive 516 to adaptively or dynamically move the object O along its axis 290 to the second position shown in FIGS. 6a-6b which results in the 3.5× magnification of the object (as well as the maximum outline of the object O more fully filling the area of the beam 222 and the centroid C being closer to or intersecting the beam axis 244.

While FIGS. 5a-5b and 6a-6b illustrate the motion control apparatus 500 moving the object O in a direction towards the source 220, other arrangements encompassed herein may include the motion control apparatus 500 moving the object O in a direction away from the source 220. As just one example, in the case where the first position of the object O and object receiving surface 216 was about halfway between the source 220 and detector 224 and the maximum outline of the object O was determined by the computing system 300 or otherwise to be greater than or otherwise extend outside of the area of the beam 222, the computing system 300 may determine that the object O needs to be moved away from the source 220 and towards the detector 224 to obtain an optimal magnification of the object O such that a substantially entirety of the maximum outline of the object O is within the area of the beam 222. Various other examples of movement of the object O within the interior chamber 208 by the motion control apparatus 500 to obtain more optimal levels of magnification and higher qualities of generated images are envisioned and encompassed herein.

With reference back to FIG. 9, the method 600 may then include rotating 628 the object O while capturing images of the object O, reconstructing 632 the images to generate a three-dimensional data set and saving the same in any appropriate memory and/or storage structure of the computing system 300, and then displaying 636 the various images (e.g., the orthogonal images, the three-dimensional image) of the object O on a display (e.g., output monitor 408 of FIG. 1) for use by personnel in analyzing the images (e.g., to verify tissue margins, to detect part defects, etc.). As discussed previously, for instance, the computing system 300 may trigger the motion control apparatus 500 to rotate the object receiving surface 216 and object O about rotation axis 508 at any appropriate angular speed and simultaneously trigger the source 220 to emit a beam 222 of electromagnetic radiation along the axis 244 through the object as it is rotating about the rotational axis 508. The computing system 300 may be configured to receive and process detected electromagnetic radiation signals from the detector 224 as the object O is rotating about the rotational axis 508 to generate a plurality of two dimensional images (e.g., several times per second or more, such as in one arrangement six frames per second) which may then be reconstructed by the computing system 300 or the like into a three-dimensional data set and a corresponding three-dimensional image of the object O.

Figure 7:
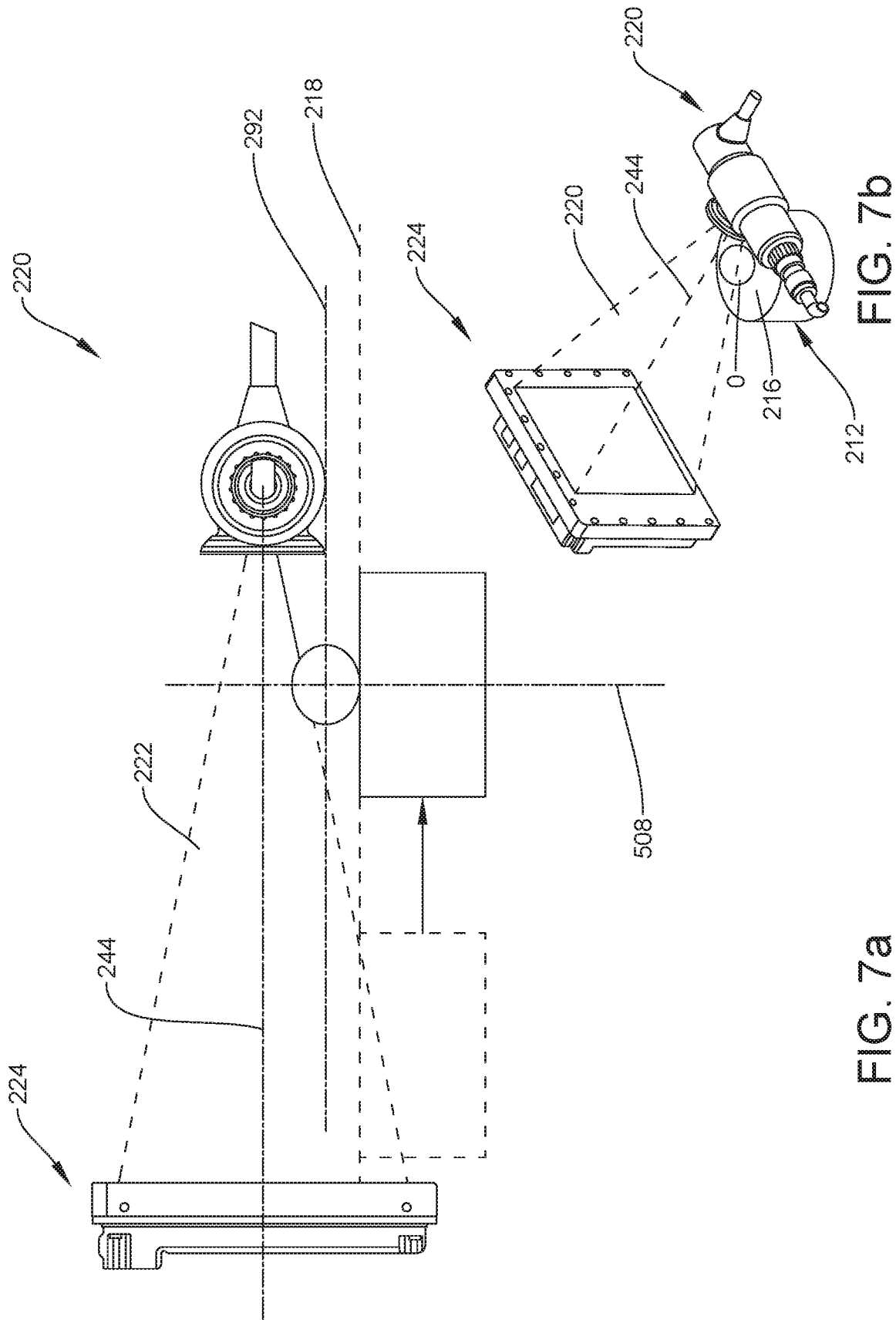
FIGS. 7a-7b and 8a-8b illustrate partial side and perspective views illustrating an object receiving surface with a specimen thereon moving from a first position to a second position relative to a source of electromagnetic radiation and an imaging detector, according to another embodiment.
Figure 8:
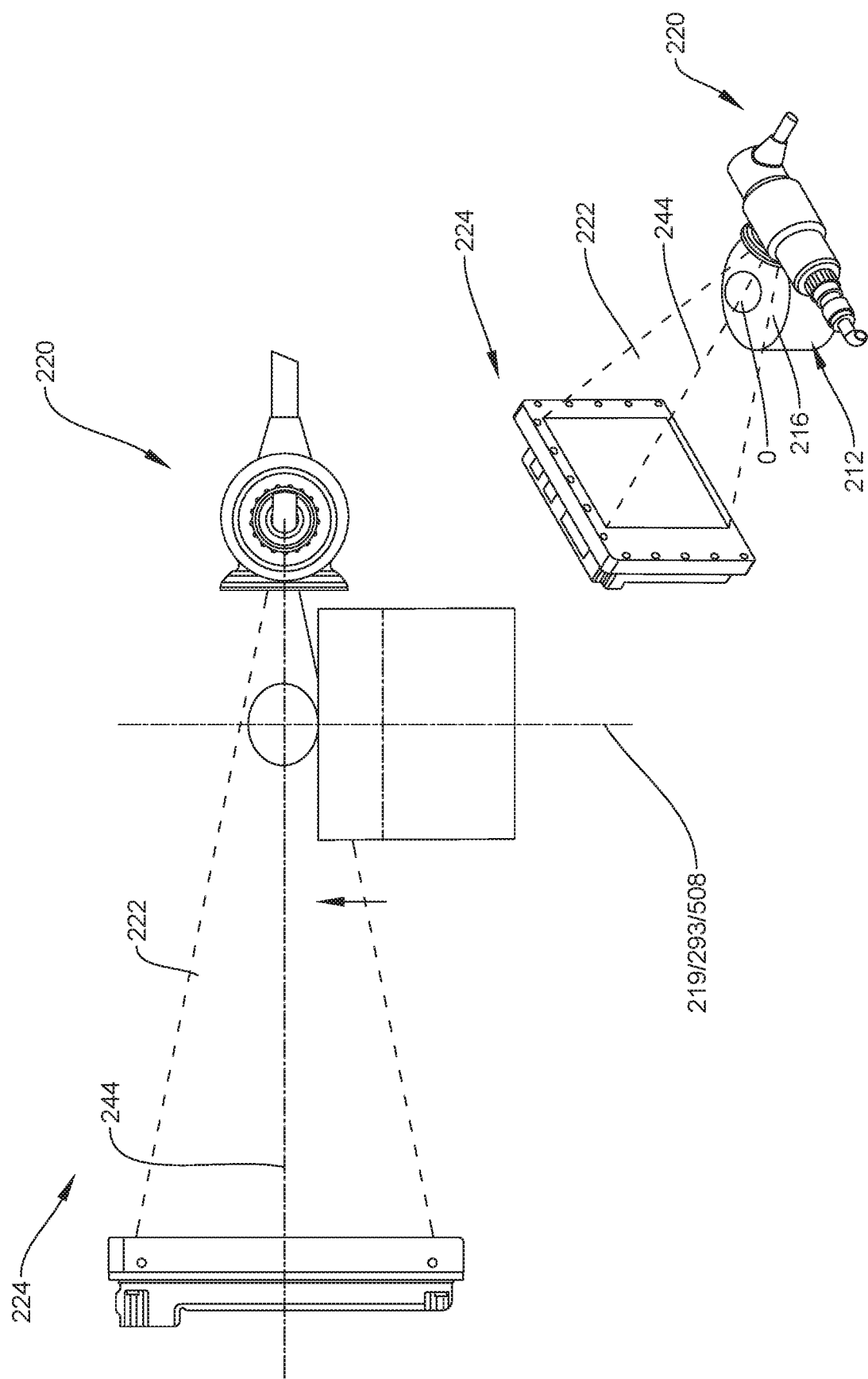

FIGS. 7a-7b and 8a-8b illustrate partial side and perspective views illustrating an object receiving surface with an object thereon moving from a first position to a second position relative to a source of electromagnetic radiation and an imaging detector, according to another embodiment. Rather than moving the object receiving surface 216 and object O along the respective axes 217, 290, the motion control apparatus 500 is configured to move the object receiving surface 216 and object O in first and second opposite directions along respective axes 218, 290 (e.g., which may be parallel to beam axis 244 as seen in FIGS. 7a-7b) and in first and second opposite directions along respective axes 219, 293 (e.g., vertically, as seen in FIGS. 8a-8b, where the axes 219, 293 may be coincident with each other and with rotation axis 508).

In this regard, and upon determination of a second position to which the object is to be moved, the computing system 300 may trigger the motion control apparatus 500 to move the object receiving surface 216 along axis 218 and/or along axis 219 to move the object receiving surface 216 and object O into their respective second positions. For instance, the embodiment of FIGS. 7a-7b and 8a-8b may be implemented by way of first and second linear drives, where the first linear drive may be similar to that illustrated in FIG. 4 but positioned such that the axis 524 of the sliding member 520 is parallel to the beam axis 244 (where the sliding member 520 is configured to orient the shaft assembly 512 perpendicular to the axis 524), and where the second linear drive is appropriately integrated with the rotary drive to slidably move the object receiving surface 216 and object O in first and second opposite directions along axes 219, 293.

In one arrangement, the computing system 300 may trigger the motion control apparatus 500 to rotate the object receiving surface 216 and object O by at least one full revolution or 360°. In other arrangements, however, the computing system 300 may trigger the motion control apparatus 500 to rotate the object receiving surface 216 and object O by more than a full revolution or even less than a full revolution (e.g., in the latter case, by 180°, by 270°, etc.), obtain a plurality of images during such rotation, and generate three-dimensional data sets for display of corresponding three-dimensional images.

While the moving step 624 was discussed as occurring after the step 620 of obtaining orthogonal images of the object, the moving step 624 may in some embodiments occur before the orthogonal imaging step 620. In some arrangements, the computing system 300 may be configured to obtain 2D (e.g., orthogonal) and 3D images of the object at two or more different magnification levels or two or more different linear positions of the object within the interior chamber 208. After obtaining 2D or 3D image data sets of the object at one magnification level or position, the computing system 300 may be configured to subsequently trigger the motion control apparatus 500 to move the specific to a different position along axis 290 whereupon the computing system 300 may then trigger the source 220 and detector 224 to obtain further image data of the object. In one arrangement, the system 100 may be configured to obtain, store and transmit high resolution digital images that are compliant with the Digital Imaging and Communications in Medicine (DICOM) standard.

Figure 10:
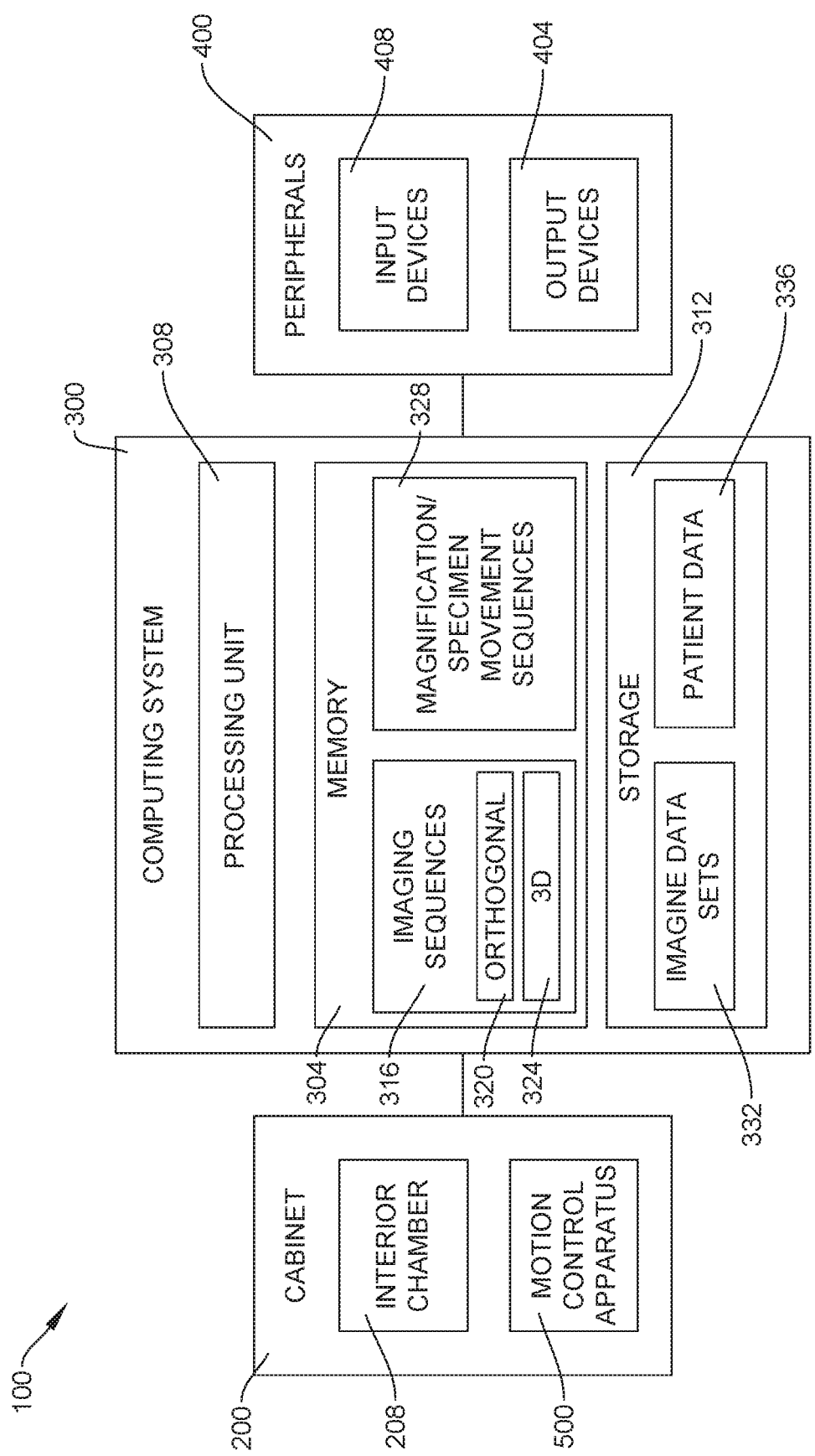
FIG. 10 is a schematic block diagram of the system of FIG. 1.

FIG. 10 presents a simplified schematic block diagram of the system 100 and illustrating some details of the computing system 300 to implement some of the functionalities disclosed herein. It is noted that not all components of the system 100 are illustrated in FIG. 10 in the interest of clarity. As shown, the computing system 300 may include at least one memory device 304 (e.g., RAM or other volatile memory), at least one processing unit 308 (e.g., processor(s), processing device(s), processor core(s), multiprocessor(s), etc.) that executes computer-readable instructions (e.g., logic, sequences, etc.) from the memory device 304, and at least one storage device 312 (e.g., hard disk, flash memory, or other non-volatile memory).

For instance, the memory device 308 may include one or more imaging sequences 316 such as orthogonal imaging sequences 320 and 3D imaging sequences 324 that are configured to be executed by the processing unit 308 to trigger the electromagnetic source 220 to emit beams of electromagnetic radiation and to collect signals from the detector 224 for use in generating and storing corresponding imaging data sets 332 in storage 312 and displaying the same on an output device 404 (e.g., monitor). The memory device 308 may also include one or more magnification/object movement sequences 328 that are configured to be executed by the processing unit 308 to trigger the motion control apparatus 500 to rotate the object receiving surface 212 and object O about rotation axis 508 and/or move object receiving surface 212 and object O along one or more of the above-discussed axes as part of imaging of the object O. Any appropriate patient data 336 (e.g., name, ID, object location, etc.) may also be stored in any appropriate format or structure.

The processing unit 308 may execute the various sequences 316, 328 independently or concurrently as appropriate, consistent with the teachings presented herein. It is to be understood that the various sequences 316, 328, etc. (logic, computer-readable instructions) may be loaded from any appropriate non-volatile storage (e.g., storage 312 or elsewhere) before being appropriately loaded into memory 304 for execution by processing unit 308. In one arrangement, the memory device 304 and processing unit 308 may function as a controller that is configured to trigger one or more components of the system 100 (e.g., motion control apparatus 500, source 220, etc.) based on inputs from a user (e.g., to initiate an imaging sequence), based on measurements or readings obtained by the computing system 300, etc.

The description herein has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. For instance, the system 100 may include any appropriate arrangement (e.g., position encoder, other indicator(s), etc.) that allows the computing system 300 to determine the angular or rotational position of the object holder 212 about the rotational axis 508. In one arrangement, the object holder 212 may be configured to be mounted to the motion control mechanism (e.g., to the shaft assembly 512) only in a particular rotational or angular position (e.g., through the use of keys and corresponding slots). In this case, and assuming an object is placed onto the object receiving surface 216 in a particular orientation relative thereto (e.g., relative to a grid or other indicator(s) on the object receiving surface 216) the computing system 300 may be able to present such object orientation information to a user on a display along with the generated images. As an example, the grid or other indicator may indicate to a user how the object is to be positioned on the object receiving surface 216 so that the computing system 300 can more accurately present such orientation information to the user on the display with the generated images. For instance, an image of a human body may be superimposed on the object receiving surface 216 to indicate to a user that the portion of the specimen closest to the patient's head should be positioned closest to the head on the superimposed human body.

In one arrangement, one or more orientation indicators or marks may be provided on or in the object holder 212 that are configured to at least partially inhibit transmission of electromagnetic radiation therethrough so that a corresponding indication or mark appears in the generated image to provide information regarding the orientation of the object relative to the indication/mark to a user (e.g., relative to a human body). In another arrangement, the computing system 300 may be configured to digitally superimpose one or more orientation indicators, marks, graphics, and/or the like into or about the generated image(s) of the object.

As mentioned, embodiments disclosed herein can be implemented as one or more computer program products, i.e., one or more modules of computer program instructions encoded on a computer-readable medium for execution by, or to control the operation of, data processing apparatus (processors, cores, etc.). The computer-readable medium can be a machine-readable storage device, a machine-readable storage substrate, a memory device, a composition of matter affecting a machine-readable propagated signal, or a combination of one or more of them. In addition to hardware, code that creates an execution environment for the computer program in question may be provided, e.g., code that constitutes processor firmware, a protocol stack, a database management system, an operating system, or a combination of one or more of them.

A computer program (also known as a program, software, software application, script, or code) used to provide the functionality described herein can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

While this disclosure contains many specifics, these should not be construed as limitations on the scope of the disclosure or of what may be claimed, but rather as descriptions of features specific to particular embodiments of the disclosure. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method of imaging a tissue specimen in a cabinet including an x-ray source and an x-ray detector positioned along a first axis, the method comprising:
    placing the tissue specimen on an object holder disposed within a chamber of the cabinet, the object holder being disposed at least partially between the x-ray source and the x-ray detector, wherein the object holder is selectively moveable in a direction along the first axis such that the object holder defines a first position;
    determining a position of the tissue specimen at the first position of the object holder relative to the x-ray source and the first axis;
    after the position of the tissue specimen at the first position is determined, moving the object holder within the chamber towards a second position based on the determined position of the tissue specimen;
    rotating the object holder around a second axis perpendicular to the first axis, wherein the object holder rotates while in the second position;
    simultaneously with rotating the object holder, emitting one or more x-ray beams along the first axis and through the tissue specimen;
    generating a plurality of two-dimensional x-ray images of the tissue specimen; and
    reconstructing the plurality of two-dimensional x-ray images into a three-dimensional data set of the tissue specimen.

2. The method of claim 1, further comprising generating a three-dimensional image of the tissue specimen from the three-dimensional data set.

3. The method of claim 2, further comprising verifying tissue margins via the three-dimensional image.

4. The method of claim 2, further comprising displaying the three-dimensional image.

5. The method of claim 1, wherein the object holder moves along a third axis that is non-parallel and non-perpendicular to the first axis.

6. The method of claim 1, further comprising:
    acquiring one or more first x-ray images of the tissue specimen when the object holder is in the first position;
    based on the one or more first x-ray images determining the position of the tissue specimen relative to the x-ray source and the first axis; and
    automatically moving the object holder towards the second position.

7. The method of claim 6, wherein the one or more first x-ray images are orthogonal images.

8. The method of claim 1, wherein the second position of the object holder causes the tissue specimen to be closer to the first axis.

9. The method of claim 1, wherein the second position of the object holder causes the tissue specimen to be closer to the x-ray source.

10. The method of claim 1, wherein the second position of the object holder causes the tissue specimen to be farther from the x-ray source.

11. A cabinet for imaging a tissue specimen comprising:
    an x-ray source;
    an x-ray detector positioned relative to the x-ray source along a first axis;
    an object holder disposed at least partially between the x-ray source and the x-ray detector and within a chamber of the cabinet, the object holder configured to receive the tissue specimen, wherein the object holder is selectively moveable in a direction along the first axis, and the object holder is rotatable around a second axis perpendicular to the first axis; and a controller operably coupled to the x-ray source, the x-ray detector, and the object holder, wherein the controller is configured to:

determine a position of the tissue specimen at a first position of the object holder relative to the x-ray source and the first axis;

after the position of the tissue specimen at the first position is determined, the controller moves the object holder within the chamber towards a second position based on the determined position of the tissue specimen;

rotate the object holder around the second axis, wherein the object holder rotates while in the second position;

simultaneously with rotating the object holder, emit one or more x-ray beams along the first axis and through the tissue specimen;

generate a plurality of two-dimensional x-ray images of the tissue specimen; and reconstruct the plurality of two-dimensional x-ray images into a three-dimensional data set of the tissue specimen.

12. The cabinet of claim 11, wherein the controller is further configured to generate a three-dimensional image of the tissue specimen from the three-dimensional data set.

13. The cabinet of claim 12, further comprising a display for displaying the three-dimensional image.

14. The cabinet of claim 13, wherein the display is included as a single unit with the cabinet.

15. The cabinet of claim 11, wherein the first position and the second position of the object holder defines a third axis that is non-parallel and non-perpendicular to the first axis.

16. The cabinet of claim 11, wherein the controller automatically moves the object holder towards the second position based on one or more first x-ray images acquired when the object holder is in the first position.

17. The cabinet of claim 11, wherein the second position of the object holder positions the tissue specimen closer to the first axis.

18. The cabinet of claim 11, wherein the second position of the object holder positions the tissue specimen closer to or further away from the x-ray source.

* * * * *